United States Patent [19]

Yamada et al.

[11] 4,229,538

[45] Oct. 21, 1980

[54] PROCESS FOR PREPARING ACYL-COA SYNTHETASE LCF-18

[75] Inventors: Hideaki Yamada; Sakayu Shimizu; Yoshiki Tani, all of Kyoto, Japan

[73] Assignee: Amano Pharmaceutical Co. Ltd., Nagoya, Japan

[21] Appl. No.: 28,604

[22] Filed: Apr. 9, 1979

[30] Foreign Application Priority Data

May 15, 1978 [JP] Japan .................................. 53-56604
Jan. 26, 1979 [JP] Japan .................................. 54-7244

[51] Int. Cl.$^3$ ............................................. C12N 9/10
[52] U.S. Cl. ..................................... 435/193; 435/15; 435/911
[58] Field of Search ................................. 435/15, 193

[56] References Cited

U.S. PATENT DOCUMENTS 4,071,413  1/1978  Takahashi et al. ................ 435/15 X

OTHER PUBLICATIONS

Estroumza et al., Chemical Abstracts vol. 72, 96873x (1970).
Ray et al., Chemical Abstracts vol. 86, 52028k (1977).
Kamiryo et al., Chemical Abstracts vol. 88, 34332s (1978).

*Primary Examiner*—Lionel M. Shapiro
*Attorney, Agent, or Firm*—Browdy and Neimark

[57] ABSTRACT

Acyl-CoA synthetase, having a high activity to $C_{16}$–$C_{18}$ long chain fatty acids, is obtained by culturing strains belonging to various genera. As is known, acyl-CoA synthetase, having a strong activity to $C_{16}$–$C_{18}$ long chain fatty acids, is generally obtained from liver of rat; however, it has now been discovered that acyl-CoA synthetase can be obtained from microorganisms and this enzyme is called acyl-CoA synthetase LCF-18. By use of acyl-CoA synthetase LCF-18 of the present invention which has a high activity to $C_{16}$–$C_{18}$ long chain fatty acids, serum non-esterified fatty acid of human beings can be accurately determined, and it is very useful for diagnosis of diabetes and so forth.

2 Claims, 4 Drawing Figures

PROCESS FOR PREPARING ACYL-COA SYNTHETASE LCF-18

FIELD OF THE INVENTION

The present invention relates to a method for the production of acyl-CoA synthetase from microorganisms, and more particularly, the present invention is concerned with a fermentative production of acyl-CoA synthetase by microorganisms, the enzyme having a high activity to $C_6$–$C_{19}$ fatty acids more particularly to $C_{16}$–$C_{18}$ long chain fatty acids.

BACKGROUND OF THE INVENTION

In general, acyl-CoA synthetase is an enzyme which thioesterifies the non-esterified fatty acid in the presence of CoA, ATP and Mg ion to make acyl-CoA, and it is also called thiokinase. This enzymatic reaction proceeds as follows:

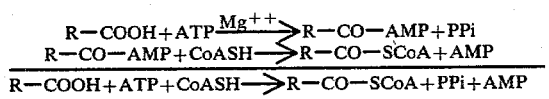

In recent years, with the solution of the physiological significance of non-esterified fatty acid in vivo, an increase and decrease of the amount of serum non-esterified fatty acid has come to be medically regarded as important. For example it has been found that an extreme increase of serum non-esterified fatty acid is recognized in case of disease of diabetes.

As a result, an increase of serum non-esterified fatty acid, detected by its determination, has come to be utilized for the diagnosis of the condition of such a disease as diabetes, but the serum non-esterified fatty acid has been generally determined by chemical colorimetric method. But the chemical colorimetric method requires a large quantity of blood, complicated analytical procedures and a longer time to perform it, resulting in this method being undesirable. Then, with the recent development of the method for clinical laboratory use, the quantitative determination method of non-esterified fatty acid by so-called enzymatic method has recently come to be used.

In order to quantitatively determine non-esterified fatty acid according to the enzymatic method, non-esterified fatty acid and acyl-CoA synthetase are reacted to form acyl-CoA and the product formed by this reaction is enzymatically determined thereby obtaining the concentration of non-esterified fatty acid. But with respect to the serum non-esterified fatty acid, since $C_{16}$–$C_{18}$ long chain fatty acids are contained in large quantities in serum, an acyl-CoA synthetase that is able to thioesterify efficiently $C_{16}$–$C_{18}$ long chain fatty acids to make acyl-CoA is naturally required. However, the acyl-CoA synthetase derived from liver microsome of rat is the only one which has been known which is fit for this purpose.

However, as this acyl-CoA synthetase is derived from an animal, it is very expensive; therefore, for economic reasons, it has been desired to derive the acyl-CoA synthetase from microorganisms which is not an expensive origin.

Heretofore, as the microorganisms being able to produce acyl-CoA synthetase, the following is known: *Escherichia coli* [European Journal of Biochemistry vol. 12, 576–582 (1970)]; *Bacillus megaterium* strain M [Biochemistry vol. 4, 85–95 (1965)]; Torulopsis $Y_8$ [Journal of Bacteriology vol. 104, 1397–1398 (1970)]; Pseudomonas 22 [Journal of Bacteriology vol. 105, 1216–1218 (1971)] and *Nocardia asteroides* [Journal of Bacteriology vol. 114, 249–256 (1973)].

But since all of these known strains produce, as substrate specificity, such an acyl-CoA synthetase that has an optimum activity to the fatty acids having fourteen and less carbon atoms in the carbon chain, such enzyme derived from these strains can not be employed for clinical laboratory determination of $C_{16}$–$C_{18}$ long chain fatty acids.

SUMMARY OF THE INVENTION

With respect to the acyl-CoA synthetase which acts on $C_{16}$–$C_{18}$ long chain fatty acids as strongly as that derived from rat liver microsome, if such a strain that produces said acyl-CoA synthetase in large quantities can be found among the enzyme producing microorganisms, there should able to be great industrial usefulness, and, from this point of view, the inventors of the present invention have pursued their studies and as a result found that strains that have such said enzymatic activity exist in a wide range amoung microorganisms, and thus completed the present invention.

DETAILED DESCRIPTION OF PREFERRED EMBODIMENTS

Figure 1:
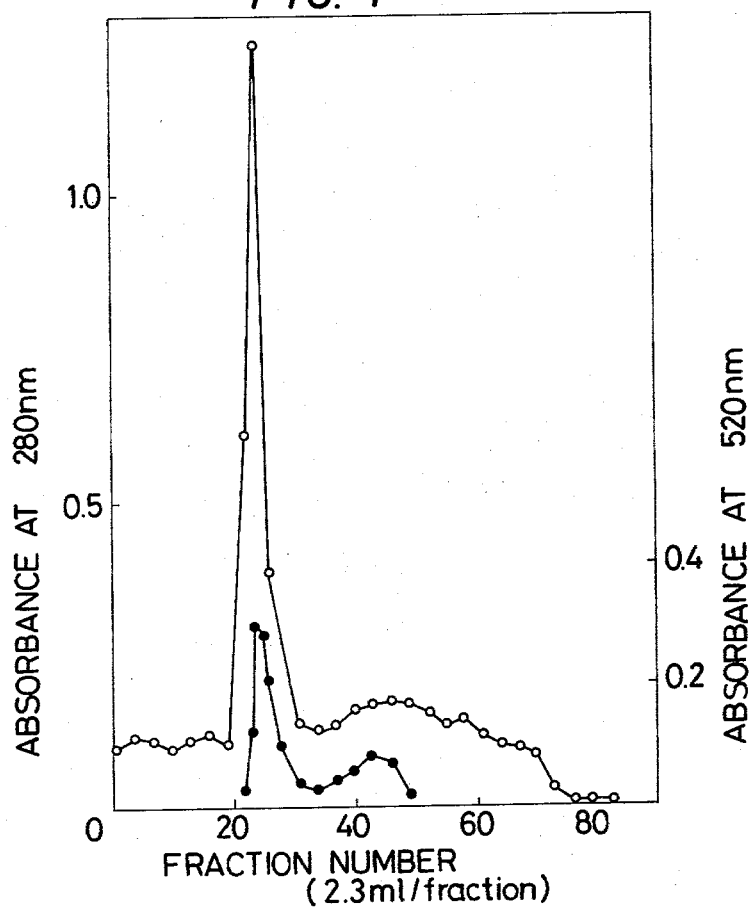
FIG. 1 is a pattern showing the partial purification of the present enzyme by Sephadex G-200 treatment.
Figure 3:
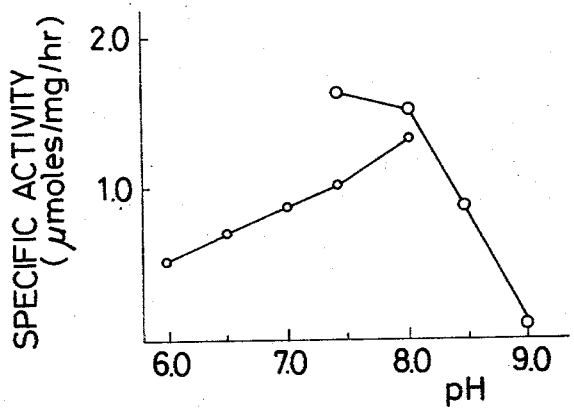
FIG. 3 and FIG. 4 are graphs showing the optimum pH and optimum temperature of the present enzyme. In, FIG. 3, in case of pH values from 6.0 to 8.0 and from 7.5 to 9.0, potassium phosphate buffer and Tris-HCl buffer were respectively used.
Figure 2:
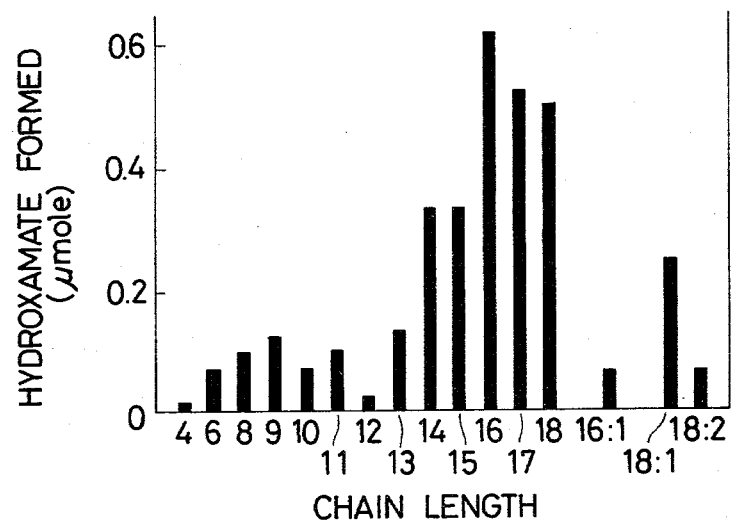
FIG. 2 is a pattern showing the substrate specificity of the present enzyme against each fatty acid having various carbon chain lengths.
Figure 4:
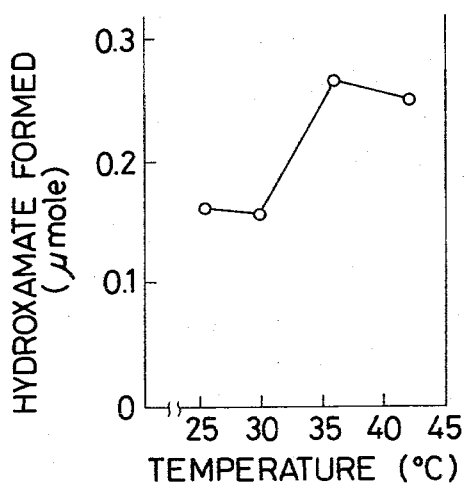

A wide range of microorganisms were screened for strains assimilable of sodium palmitate as a source of carbon. Each strain growable in the sodium palmitate medium was then cultivated in a medium (pH 7.0) containing sodium palmitate 1%, peptone 0.2%, $K_2HPO_4$ 0.1%, $KH_2PO_4$ 0.1%, $MgSO_4.7H_2O$ 0.05%. The yeast extract 0.03% and Triton X-100 0 to 1.0%, and thus cultured cells were then suspended in 0.02 M potassium phosphate buffer (pH 8) containing 10 mM 2-mercaptoethanol, and disrupted by ultrasonic oscillator to extract acyl-CoA synthetase. The enzymatic activity of palmitolyl-CoA synthetase was then examined. Table 1 shows several strains among those having said enzymatic activity strongly.

The activity of stearyl-CoA synthetase and that of palmitoyl-CoA synthetase of these strains were nearly same.

Table 1

| Strain | | Activity of palmitoyl-CoA synthetase ($\mu$mole/mg/h) |
|---|---|---|
| *Escherichia intermedia* | IFO 13545 | 0.044 |
| *Aerobacter cloacae* | IAM 1221 | 0.029 |
| *Aerobacter aerogenes* | IFO 3318 | 0.029 |
| *Serratia marcescens* | IFO 3054 | 0.064 |
| *Proteus mirabilis* | IFO 3849 | 0.026 |
| *Salmonella typhimurium* | IFO 13245 | 0.030 |
| *Staphylococcus aureus* | IFO 3060 | 0.034 |
| *Corynebacterium paurometabolum* | IFO 12160 | 0.020 |

Table 1-continued

| Strain | | Activity of palmitoyl-CoA synthetase (μmole/mg/h) |
|---|---|---|
| Pseudomonas aeruginosa | IFO 3919 | 0.149 |
| Pseudomonas fluorescens | IFO 3903 | 0.048 |
| Pseudomonas docunhae | IFO 12048 | 0.040 |
| Pseudomonas schuylkilliensis | IFO 12055 | 0.055 |
| Pseudomonas marginalis | IFO 3925 | 0.022 |
| Pseudomonas cruciviae | IFO 12047 | 0.037 |
| Pseudomonas synxantha | IFO 3906 | 0.077 |
| Pseudomonas taetralens | IFO 12691 | 0.022 |
| Aeromonas hydrophila | IFO 3820 | 0.057 |
| Aeromonas liquefaciens | IFO 12978 | 0.042 |
| Streptomyces rimosus | IFO 3441 | 0.036 |
| Aspergillus sojae | IFO 4279 | 0.033 |
| Aspergillus terreus | IFO 7078 | 0.025 |
| Penicillium javanicum | IFO 4639 | 0.047 |
| Fusarium oxysporum | IFO 5942 | 0.058 |
| Gibberella fujikuroi | IFO 6604 | 0.080 |
| Candida guilliermondii | IFO 0566 | 0.025 |
| Candida lipolytica | IFO 0717 | 0.123 |
| Candida tropicalis | IFO 1070 | 0.029 |

Moreover, among the strains of Basidiomycetes, a screening was performed in a wide range for strains assimilable of glucose and/or sodium palmitate as carbon source, and then each strain was cultivated, grown in the medium above, respectively in the following media:

One medium (pH 4.5) (glucose medium: hereinafter designated as G-medium) containing yeast extract 0.5%, glucose 2.0% and tap water;

the other medium (pH 4.5) (glucose-sodium palmitate medium: hereinafter designated as G+P medium) consisting of such one prepared by adding 0.5% of sodium palmitate to G-medium.

The thus cultured cells were suspended respectively in 0.02 M potassium phosphate buffer (pH 6.5) containing 10 mM 2-mercaptoethanol, the cells were disrupted respectively by ultrasonic oscillator to extract acyl-CoA synthetase, and acyl-CoA synthetase thus obtained was examined for the activity of palmitoyl-CoA synthesis. Table 2 shows several strains among those having said enzymatic activity strongly.

The activity of stearyl-CoA synthesis of this acyl-CoA synthetase and that of palmitoyl-CoA synthesis were nearly same.

Table 2

| Strain | Activity of palmitoyl CoA synthetase (μmole/mg/hr) | |
|---|---|---|
| | (G) | (G + P) |
| Gloeophyllum sepiarium IFO 4944 | .290 | — |
| Trametes gibbosa IFO 4946 | <.200 | <.200 |
| Gloeophyllum sepiarium IFO 6267 | .318 | .358 |
| Gloeophyllum trabeum IFO 6429 | .182 | .362 |
| Gloeophyllum trabeum IFO 6430 | .397 | <.200 |
| Gloeophyllum ungulatum IFO 6431 | .262 | .482 |
| Daedalea dickinsii IFO 6488 | <.200 | <.200 |
| Laetiporus sulphureus IFO 6497 | <.200 | <.200 |
| Gloeophyllum striatum IFO 6506 | <.200 | <.200 |
| Gloeophyllum unglatum IFO 6507 | — | <.200 |
| Gloeophyllum trabeum IFO 6509 | .236 | — |
| Flammulina velutipes IFO 8329 | <.200 | <.200 |
| Lentinus edodes IFO 8340 | <.200 | <.200 |
| Lenzites belutina IFO 8715 | <.200 | <.200 |
| Pycnoporus coccineus IFO 9768 | <.200 | .224 |
| Tyromyces palustris IFO 30339 | <.200 | <.200 |
| Coriolus versicolor IFO 30338 | <.200 | <.200 |
| Trametes sanguinea IFO 6489 | .333 | .421 |
| Trametes sanguinea IFO 6490 | .250 | .421 |
| Trametes sanguinea IFO 6491 | .246 | <.200 |
| Schizophyllum commune IFO 4928 | <.200 | <.200 |
| Schizophyllum commune IFO 4929 | <.200 | <.200 |
| Schizophyllum commune IFO 6502 | <.200 | .220 |
| Schizophyllum commune IFO 6503 | <.200 | <.200 |
| Schizophyllum commune IFO 6504 | <.200 | <.200 |

As obvious from the results shown in Tables 1 and 2, the microorganisms which are able to produce palmitoyl-CoA synthetase are the strains belonging to the following genera: Genus Escherichia, Aerobacter, Serratia, Proteus, Salmonella, Staphylococcus, Corynebacterium, Pseudomonas, Aeromonas, Streptomyces, Aspergillus, Penicillium, Fusarium, Gibberella, Candida, Gloeophyllum, Trametes, Daedalea, Laetiporus, Flammulina, Lentinus, Lenzites, Pycnoporus, Tyromyces, Coriolus and Schizophyllum.

Moreover, such microorganisms are able to be concretely exemplified by the following species: Pseudomonas aeruginosa IFO 3919, Pseudomonas synxantha IFO 3906, Pseudomonas schuylkilliensis IFO 12055, Candida lipolytica IFO 0717, Gibberella fujikuroi IFO 6604, Fusarium oxysporum IFO 5942, Serratia marcescens IFO 3054, Aeromonas hydrophila IFO 3820, Gloeophyllum seprarium IFO 6267, Gloeophyllum trabeum IFO 6430, Gloeophyllum ungulatum IFO 6431, Pycnoporus coccineus IFO 9768, Trametes sanguinea IFO 6489 and Gloeophyllum trabeum IFO 6509.

All of these strains are stored in IFO (Institute for Fermentation, Osaka), open to the public and are freely available.

As a medium to be used, both natural medium and synthetic medium containing sources of carbon, nitrogen and inorganic salts and sources of other nutrients in addition, can be widely used. As sources of carbon, the following can be used: $C_4$–$C_8$ fatty acids, for example, oleic acid, palmitic acid, linoleic acid, etc. and salts thereof, for example, sodium salt, potassium salt, etc., as well as glucose, fructose, galactose, glycerol, citrate, sorbitol or any other commonly used carbon source.

As sources of nitrogen, the following can be used: inorganic nitrogen compounds such as sodium nitrate, ammonium sulfate, ammonium chloride etc. or organic nitrogen compounds such as peptone, meat extract, corn steep liquor, yeast extract, etc. As inorganic salts, $KH_2PO_4$, $MgSO_4$, etc. can be used, and in addition to this, Triton X-100 is used as surface active agent.

A preferred composition of the medium to carry out the present invention is exemplified by the following:

sodium palmitate 1.0%, peptone 0.3%, $K_2HPO_4$ 0.1%, yeast extract 0.03% and $MgSO_4.7H_2O$ 0.05%. As culturing conditions, the strain may be advantageously cultured at 22°–37° C. for 2–7 days under aerobic conditions.

The fermentation broth thus obtained is centrifuged or filtrated at reduced pressure to obtain cells, thus obtained cells are disrupted by ultrasonic oscillator (6 min., at 15° C. and below), and moreover they are subjected to a centrifugal separation to obtain supernatant. Then from said supernatant acyl-CoA synthetase is purified according to the following procedure. First of all, said supernatant, namely crude enzyme solution, is fractionated from ammonium sulfate (30–45% saturation), then is applied to a Sephadex G-200 column, and furthermore the active fractions are fractionated by 30–50% saturation with ammonium sulfate, and then are subjected to a DEAE-cellulose and a Sephadex G-200 treatments, so that acyl-CoA synthetase is obtained. Physical and chemical properties of acyl-CoA synthetase thus obtained are as follows:

1. Substrate specificity:

This enzyme acts on $C_6$–$C_{19}$ carbon chain fatty acids especially on $C_{16}$–$C_{18}$ long chain fatty acids to produce respectively acyl-CoA synthetase according to the used fatty acid.

2. Optimum pH:

The optimum pH of the present enzyme is near 7–8.

3. Optimum temperature:

The optimum temperature of the present enzyme is 35°–45° C.

4. Stability:

The present enzyme is stable in the solution (pH 7.4) of 0.02 M Tris-HCl buffer containing 10 mM 2-mercaptoethanol at 5° C. and below for 7 days, and furthermore it is stable for 1 month and more in the presence of glycerol at final concentration of 50%.

5. Effect of Inhibitor etc.

A high concentration of water soluble long chain fatty acid, such as lauric acid, oleic acid, palmitooleic acid, etc., inhibits extremely the reaction. But this inhibitory action is reduced in case of coexistence of serum albumin.

Activity of the present enzyme was determined in accordance with the method of Kornberg-Pricer [Journal of Biological Chemistry vol. 204, 329–343 (1953)] by using long chain fatty acids such as palmitate ($C_{16}$) or stearate ($C_{18}$) as substrate.

An activity (specific activity) is represented by the amount of hydroxamate (μmole) which is produced by 1 mg of enzyme protein per hour.

Acyl-CoA synthetase obtained according to the present invention has a characteristic of acting on $C_{16}$–$C_{18}$ long chain fatty acids just like as the acyl-CoA synthetase derived from rat liver microsome. This is the first time that such acyl-CoA synthetase has ever been discovered from microorganisms, so the acyl-CoA synthetase according to the present invention is called acyl-CoA synthethase LCF-18.

Acyl-CoA synthetase LCF-18 is obtained from microorganisms, therefore it is possible to produce it on a large industrial scale, and since it has a strong activity to $C_{16}$–$C_{18}$ long chain fatty acids, it is extremely useful for determination of human serum non-esterified fatty acid.

The quantitative determination method of serum non-esterified fatty acid by employing acyl-CoA synthetase LCF-18 is as follows:

Reacting acyl-CoA synthetase LCF-18 with serum non-esterified fatty acid in the presence of ATP and CoA, reacting myokinase with thus formed AMP in the presence of ATP, reacting pyruvate kinase with thus formed ADP in the presence of phosphoenol-pyruvate, and then reacting lactate dehydrogenase with thus formed pyruvate in the presence of NADH, and in consequence NADH being allowed to change into NAD, then the concentration of the resultant reduced NADH is measured at 340 nm. This reaction may be illustrated by the following equations (1) to (4):

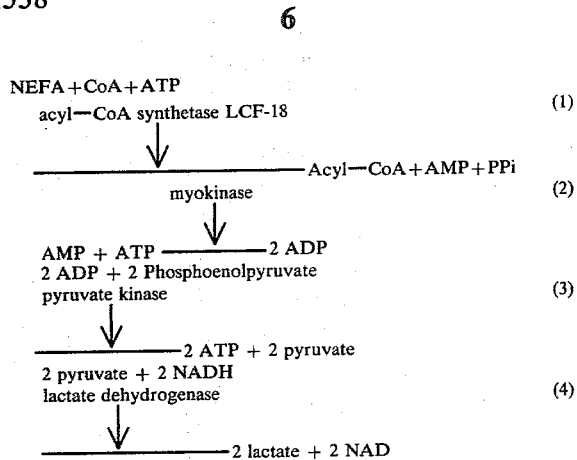

According to the present method, the accurate quantitative determination of serum non-esterified fatty acid can be performed, and the diagnosis of diabetes etc. can be easily performed.

Next, the present invention is described in the following Examples.

EXAMPLE 1

500 ml Sakaguchi flasks each containing 200 ml of a main medium are prepared. The main medium (10 l, pH 6.4) is composed of 0.5% of succinate, 0.3% of peptone, 0.1% of $K_2HPO_4$, 0.03% of yeast extract and 0.05% of $MgSO_4.7H_2O$, and it is sterilized for 20 minutes at 120° C. prior to use. Each flask is inoculated with 2 ml of a seed culture liquid of Pseudomonas aeruginosa IFO 3919 which has been previously obtained by seeding said strain in a seed medium (pH 6.4) composed of 1% of glucose, 1.5% of peptone, 0.3% of $K_2HPO_4$ and 0.02% of $MgSO_4.7H_2O$, followed by the incubation thereof. The flask is incubated at 28° C. for 24 hours under aerobic conditions; thereafter the culture broth thus obtained is centrifuged to obtain 45 g of the wet cells. Said wet cells are added with 100 ml of 0.02M potassium phosphate buffer (pH 8.0) containing 10 mM 2-mercaptoethanol, disrupted by ultrasonic oscillator, and then centrifuged (at 25000×G), and as a result, 96 ml of a supernatant is obtained. This supernatant shows a specific activity of acyl-CoA synthetase of 0.230 μmoles/mg/hour as palmitoyl-CoA synthetase activity.

EXAMPLE 2

500 ml Sakaguchi flasks each containing 200 ml of a main medium are prepared. The main medium (10 l, pH 6.4) is composed of 1.0% of sodium palmitate, 0.3% of peptone, 0.1% of $K_2HPO_4$, 0.03% of yeast extract and 0.05% of $MgSO_4$. $7H_2O$, and it is sterilized for 20 minutes at 120° C. prior to use. Each flask is inoculated with 2 ml of a seed culture liquid of Candida lipolytica IFO 0717 which has been previously obtained by seeding said strain in a seed medium (pH 6.4) composed of 1% of glucose, 1.5% of peptone, 0.3% of $K_2HPO_4$ and 0.02% of $MgSO_4.7H_2O$, followed by the incubation thereof. The flask is incubated at 28° C. for 24 hours under aerobic conditions; thereafter the culture broth thus obtained is centrifuged to give 48 g of wet cells. Said wet cells are added with 100 ml of 0.02 M potassium phosphate buffer (pH 8.0) containing 10 mM 2-mercaptoethanol, 1% of Triton X 100, 1 mM $MgCl_2$ and 1 mM EDTA, disrupted by ultrasonic oscillator (for 6 minutes, at 15° C. and below), followed by centrifugal separation (at 12000×G) to yield 98 ml of supernatant. Thus obtained supernatant has the specific activity of acyl-CoA synthetase of 0.12 µmoles/mg/hour as palmitoyl-CoA synthetase activity.

EXAMPLE 3

500 ml Sakaguchi flasks each containing 200 ml of a main medium are prepared. The main medium (10 l, pH 7.0) is composed of 0.5% of glucose, 0.5% of sodium palmitate, 0.3% of peptone, 0.1% of $K_2HPO_4$, 0.03% of yeast extract and 0.05% of $MgSO_4.7H_2O$, and it is sterilized for 20 minutes at 120° C. prior to use. Each flask is inoculated with 2 ml of a seed culture liquid of *Gibberella fujikuroi* IFO 6604 which has been previously obtained by seeding said strain in a seed medium (pH 7.0) composed of 1% of glucose, 1.5% of peptone, 0.3% of $K_2HPO_4$ and 0.02% of $MgSO_4.7H_2O$, followed by the incubation thereof. The flask is incubated at 30° C. for 24 hours under aerobic conditions; thereafter the culture broth thus obtained is centrifuged to give 45 g of wet cells. Thus obtained wet cells are added with 100 ml of 0.02 M potassium phosphate buffer (pH 8.0) containing 10 mM 2-mercaptoethanol, disrupted by ultrasonic oscillator (for 6 minutes, at 15° C. and below), and then centrifuged (at 25000×G) to yield 95 ml of supernatant. Thus obtained supernatant shows a specific activity of acyl-CoA synthetase of 0.142 µmoles/mg/hour as palmitoyl-CoA synthetase activity.

EXAMPLE 4

Similarly as in Example 1, *Pseudomonas synxantha* IFO 3906 is cultivated to obtain 40 g of wet cells. Thus obtained wet cells are added with 100 ml of 0.02 M potassium phosphate buffer (pH 8.0) containing 10 mM 2-mercaptoethanol, disrupted by ultrasonic oscillator (for 6 minutes, at 15° C. and below), followed by the centrifugal separation (at 25000×G) to yield 90 ml of supernatant. Thus obtained supernatant shows a specific activity of acyl-CoA synthetase of 0.180 µmoles/mg/hour as palmitoyl-CoA synthetase activity.

EXAMPLE 5

Similarly as in Example 2, *Fusarium oxysporum* IFO 5942 is cultivated to obtain 40 g of wet cells. Thus obtained 100 ml of 0.02 M potassium phosphate buffer (pH 8.0) containing 10 mM 2-mercaptoethanol, 1% of Triton X 100, 1 mM $MgCl_2$ and 1 mM EDTA, disrupted by ultrasonic oscillator (for 6 minutes, at 15° C. and below), and then centrifuged (at 12000×G) to yield 95 ml of supernatant. Thus obtained supernatant has a specific activity of acyl-CoA synthetase of 0.15 µmoles/mg/hour as palmitoyl-CoA synthetase activity.

EXAMPLE 6

Similarly as in Example 2, *Serratia marcescens* IFO 3054 is cultivated to obtain 43 g of wet cells. Thus obtained wet cells are added with 100 ml of 0.02 M potassium phosphate buffer (pH 8.0) containing 10 mM 2-mercaptoethanol, 1% of Triton X 100, 1 mM $MgCl_2$ and 1 mM EDTA, disrupted by ultrasonic oscillator (for 6 minutes, at 15° C. and below), followed by the centrifugal separation (at 12000×G) to yield 95 ml of supernatant. Thus obtained supernatant has a specific activity of acyl-CoA synthetase of 0.075 µmoles/mg/hour as palmitoyl-CoA synthetase activity.

EXAMPLE 7

Similarly as in Example 1, *Aeromonas hydrophila* IFO 3820 is cultivated to obtain 42 g of wet cells. Thus obtained wet cells are added with 100 ml of 0.02 M potassium phosphate buffer (pH 8.0) containing 10 mM 2-mercaptoethanol, disrupted by ultrasonic oscillator (for 6 minutes, at 15° C. and below), followed by the centrifugal separation (at 25000×G) to yield 98 ml of supernatant. Thus obtained supernatant has a specific activity of acyl-CoA synthetase of 0.057 µmoles/mg/hour as palmitoyl-CoA synthetase activity.

EXAMPLE 8

Similarly as in Example 1, *Pseudomonas schuylkilliensis* IFO 12055 is cultivated to obtain 40 g of wet cells. Thus obtained wet cells are added with 100 ml of 0.02 M potassium phosphate buffer (pH 8.0) containing 10 mM 2-mercaptoethanol, disrupted by ultrasonic oscillator (for 6 minutes, at 15° C. and below), followed by the centrifugal separation (at 25000×G) to yield 95 ml of supernatant. Thus obtained supernatant has the specific activity of acyl-CoA synthetase of 0.055 µmoles/mg/hour as palmitoyl-CoA synthetase activity.

EXAMPLE 9

500 ml Sakaguchi flasks each containing 200 ml of a main medium are prepared. The main medium (10 l, pH 4.5) is composed of 2.0% of glucose, 0.5% of sodium palmitate, 0.3% of peptone, 0.1% of $K_2HPO_4$, 0.5% of yeast extract and 0.05% of $MgSO_4.7H_2O$, and it is sterilized for 20 minutes at 120° C. prior to use. Each flask is inoculated with 2 ml of a seed culture liquid of *Gloeophyllum sepiarium* IFO 6267 which has been previously obtained by seeding said strain in a seed medium (pH 4.5) composed of 1% of glucose, 1.5% of peptone, 0.3% of $K_2HPO_4$ and 0.02% of $MgSO_4.7H_2O$, followed by the incubation thereof. The flask is incubated at 28° C. for 5 days under aerobic conditions; thereafter the culture broth thus obtained is filtrated at reduced pressure to give 45 g of wet cells. Thus obtained wet cells are added with 100 ml of 0.02 M potassium phosphate buffer (pH 6.5) containing 10 mM 2-mercaptoethanol, disrupted by ultrasonic oscillator (for 6 minutes, at 15° C. and below), and then centrifuged (at 25000×G) to yield 96 ml of supernatant. Thus obtained supernatant has a specific activity of acyl-CoA synthetase of 0.358 µmoles/mg/hour as palmitoyl-CoA synthetase activity.

EXAMPLE 10

500 ml Sakaguchi flasks each containing 200 ml of a main medium are prepared. The main medium (10 l, pH 4.5) is composed of 2.0% of glucose, 0.3% of peptone, 0.1% of $K_2HPO_4$, 0.5% of yeast extract and 0.05% of $MgSO_4.7H_2O$, and it is sterilized for 20 minutes at 120° C. prior to use. Each flask is inoculated with 2 ml of a seed culture liquid of *Gloeophyllum trabeum* IFO 6430 which has been previously obtained by seeding said strain in a medium (pH 4.5) composed of 1% of glucose, 1.5% of peptone, 0.3% of $K_2HPO_4$ and 0.02% of $MgSO_4.7H_2O$, followed by the incubation thereof. The flask is incubated at 28° C. for 5 days under aerobic conditions; thereafter the culture broth thus obtained is filtrated at reduced pressure to give 48 g of wet cells. Thus obtained wet cells are added with 100 ml of 0.02 M potassium phosphate buffer (pH 6.5) containing 10 mM 2-mercaptoethanol, 1% of Triton X-100, 1 mM $MgCl_2$ and 1 mM EDTA, disrupted by ultrasonic oscillator (for 6 minutes, at 15° C. and below), and then centrifuged (at 12000×G) to yield 98 ml of supernatant. Thus obtained supernatant shows acyl-CoA synthetase specific activity of 0.397 μmoles/mg/hour as palmitoyl-CoA synthetase activity.

EXAMPLE 11

Similarly as in Example 9, *Gloeophyllum ungulatum* IFO 6431 is cultivated to obtain 40 g of wet cells. Thus obtained wet cells are added with 100 ml of 0.02 M potassium phosphate buffer (pH 6.5) containing 10 mM 2-mercaptoethanol, disrupted by ultrasonic oscillator (for 6 minutes, at 15° C. and below), followed by the centrifugal separation (at 25000×G) to yield 90 ml of supernatant. Thus obtained supernatant shows acyl-CoA synthetase specific activity of 0.482 μmoles/mg/hour as palmitoyl-CoA synthetase activity.

EXAMPLE 12

Similarly as in Example 10, *Gloeophyllum trabeum* IFO 6509 is cultivated to obtain 40 g of wet cells. Thus obtained wet cells are added with 0.02 M potassium phosphate buffer (pH 6.5) containing 10 mM 2-mercaptoethanol, 1% of Triton X-100, 1 mM $MgCl_2$ and 1 mM EDTA, disrupted by ultrasonic oscillator (for 6 minutes, at 15° C. and below), and then centrifuged (at 12000×G) to yield 95 ml of supernatant. Thus obtained supernatant has a specific activity of acyl-CoA synthetase of 0.236 μmoles/mg/hour as palmitoyl-CoA synthetase activity.

EXAMPLE 13

Similarly as in Example 9, *Pycnoporus coccineus* IFO 9768 is cultivated to obtain 42 g of wet cells. Thus obtained wet cells are added with 100 ml of 0.02 M potassium phosphate buffer (pH 6.5) containing 10 mM 2-mercaptoethanol, disrupted by ultrasonic oscillator (for 6 minutes, at 15° C. and below), followed by the centrifugal separation (at 25000×G) to yield 98 ml of supernatant. Thus obtained supernatant shows a specific activity of acyl-CoA synthetase of 0.224 μmoles/mg/hour as palmitoyl-CoA synthetase activity.

EXAMPLE 14

Similarly as in Example 9, *Trametes sanguinea* IFO 6489 is cultivated to obtain 40 g of wet cells. Thus obtained wet cells are added with 100 ml of 0.02 M potassium phosphate buffer (pH 6.5) containing 10 mM 2-mercaptoethanol, disrupted by ultrasonic oscillator (for 6 minutes, at 15° C. and below), followed by the centrifugal separation (at 25000×G) to yield 95 ml of supernatant. Thus obtained supernatant shows a specific activity of acyl-CoA synthetase of 0.421 μmoles/mg/hour as palmitoyl-CoA synthetase activity.

EXAMPLE 15

500 ml of acyl-CoA synthetase containing liquid (palmitoyl-CoA synthetase activity of 0.230 μmoles/mg/hr) obtained in Example 1 was fractionated with ammonium sulfate (25–45% saturation), followed by dialysis against 0.02 M potassium phosphate buffer. The dialyzed solution was applied to a DEAE-cellulose column (11×25 cm) equilibrated with the same buffer. After the column was washed with 0.02 M potassium phosphate buffer, pH 8.0, containing 0.075 M KCl (6 liter), the enzyme was eluted with 0.02 M potassium phosphate buffer, pH 8.0, containing 0.3 M KCl. Active fractions were fractionated with ammonium sulfate (30–50% saturation); which was passed through a Sephadex G-200 column (3.5×105 cm) equilibrated with 0.02 M potassium phosphate buffer, pH 8.0. The enzyme was concentrated by ultrafiltration (Carl Schleicher and Schüll, Dassel), dialyzed against 0.005 M potassium phosphate buffer, pH 7.0, and applied to a hydroxylapatite column (3.5×10 cm) equilibrated with the same buffer. Elution was carried out by a linear gradient of the potassium phosphate buffer (0.02–0.4 M, 500 ml). Active fractions were concentrated as above, dialyzed against 0.02 M potassium phosphate buffer, pH 8.0, and mixed with 4/10 volume of glycerol. The final preparation had the specific activity of 60-fold against cell-free extract with the yield of 26%. The enzyme was stable at least for 4 months when stored at −20° C.

What is claimed is:

1. A process for preparing acyl-CoA synthetase LCF-18 comprising cultivating an acyl-CoA synthetase LCF-18 producing strain selected from the group consisting of Genera Gloeophyllum, Trametes, Daedalea, Laetiporus, Flammulina, Lentinus, Lenzites, Pycnoporus, Tyromyces, Coriolus and Schyzophyllum, and then isolating the enzyme of acyl-CoA synthetase LCF-18 from the thus cultured cells.

2. A process as in claim 1 wherein the acyl-CoA synthetase LCF-18 producing microorganism is selected from the group consisting of *Gloeophyllum sepiarium*, *Gloeophyllum trabeum*, *Gloeophyllum ungulatum*, *Pycnoporus coccineus*, and *Trametes sanguinea*.

* * * * *